(12) United States Patent
Castro et al.

(10) Patent No.: US 10,376,448 B2
(45) Date of Patent: Aug. 13, 2019

(54) METHOD FOR APPLYING A FOAMING COSMETIC COMPOSITION

(71) Applicant: ELC Management LLC, Melville, NY (US)

(72) Inventors: John R. Castro, Huntington Station, NY (US); Arlene G. Ting-Jenulis, Smithtown, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 541 days.

(21) Appl. No.: 14/493,594

(22) Filed: Sep. 23, 2014

(65) Prior Publication Data

US 2015/0086488 A1    Mar. 26, 2015

Related U.S. Application Data

(60) Provisional application No. 61/881,634, filed on Sep. 24, 2013.

(51) Int. Cl.
| | | |
|---|---|---|
| *A61K 8/04* | (2006.01) | |
| *A61K 8/365* | (2006.01) | |
| *A61K 8/36* | (2006.01) | |
| *A61K 8/81* | (2006.01) | |
| *A61Q 1/10* | (2006.01) | |

(52) U.S. Cl.
CPC .............. *A61K 8/046* (2013.01); *A61K 8/361* (2013.01); *A61K 8/365* (2013.01); *A61K 8/8152* (2013.01); *A61Q 1/10* (2013.01); *A61K 2800/222* (2013.01); *A61K 2800/43* (2013.01)

(58) Field of Classification Search
None
See application file for complete search history.

(56) References Cited

U.S. PATENT DOCUMENTS

| | | |
|---|---|---|
| 5,248,495 A | 9/1993 | Patterson et al. |
| 5,334,325 A | 8/1994 | Chaussee |
| 6,096,702 A | 8/2000 | Ramirez et al. |
| 7,837,984 B2 | 11/2010 | McNamara |
| 7,837,985 B2 | 11/2010 | McNamara et al. |
| 7,846,424 B2 | 12/2010 | McNamara et al. |
| 2003/0224955 A1 | 12/2003 | Ribery et al. |
| 2004/0002550 A1 | 1/2004 | Mercurio |
| 2004/0170590 A1* | 9/2004 | Fahnestock et al. ...... 424/70.14 |
| 2006/0088486 A1 | 4/2006 | McNamara et al. |
| 2006/0147399 A1* | 7/2006 | McNamara et al. ............ 424/63 |
| 2007/0148114 A1 | 6/2007 | Jager Lezer et al. |
| 2007/0189989 A1 | 8/2007 | Cantwell et al. |
| 2008/0044445 A1 | 2/2008 | Rubin |
| 2010/0074928 A1* | 3/2010 | Elliott et al. ................. 424/401 |

FOREIGN PATENT DOCUMENTS

| | | |
|---|---|---|
| EP | 1067902 B1 | 4/2003 |
| WO | WO-96/19189 | 6/1996 |
| WO | WO-2007/078460 | 7/2007 |
| WO | WO-2009/080628 | 7/2009 |

OTHER PUBLICATIONS

PCT International Search Report; International Application No. PCT/US2014/057133; Completion Date: Dec. 29, 2014; dated Dec. 29, 2014.
PCT International Search Report; International Application No. PCT/US2014/057154; Completion Date: Dec. 29, 2014; dated Dec. 30, 2014.
PCT Written Opinion of the International Searching Authority; International Application No. PCT/US2014/057133; Completion Date: Dec. 29, 2014; dated Dec. 29, 2014.
PCT Written Opinion of the International Searching Authority; International Application No. PCT/US2014/057154; Completion Date: Dec. 29, 2014; dated Dec. 30, 2014.

* cited by examiner

*Primary Examiner* — David J Blanchard
*Assistant Examiner* — Sarah J Chickos
(74) *Attorney, Agent, or Firm* — Idris McKelvey

(57) ABSTRACT

The invention relates to a method for applying a cosmetic composition to hair. The method comprises the steps of removing a cosmetic composition from a sealed container, the composition comprising: a post-foaming emulsion comprising a weak acid, a weak base, a fatty acid, and a volatile buffering agent; a film forming agent; and an aqueous carrier; applying said composition to one or more eyelashes; and during or after said application to said one or more eyelashes, said cosmetic composition forms a foam, said foam resulting from the release of a gas, said gas being a reaction product of said post-foaming emulsion, and said reaction commencing after the evaporation of said volatile buffering agent, upon exposure of said cosmetic composition to atmospheric conditions.

16 Claims, No Drawings

METHOD FOR APPLYING A FOAMING COSMETIC COMPOSITION

CROSS-REFERENCE TO RELATED APPLICATIONS

The present application claims priority from U.S. Provisional Application No. 61/881,634, filed Sep. 24, 2013.

TECHNICAL FIELD

The invention is in the field of foaming cosmetic compositions. In particular, the invention is useful for foaming mascara compositions.

BACKGROUND OF THE INVENTION

Often, women who use mascara wish to obtain the appearance of thicker lashes. Achieving lash thickness with mascara often requires multiple applications. This in turn promotes lash clumping.

Other ways to solve this problem involve lash coatings that foam when applied to the lashes. Film formers in the compositions act to affix the foamed composition to the lashes. For example, U.S. Patent Publication No. 2007/0148114 teaches foamed compositions for application to eyelashes where the foam has a very specific density of less than 0.95 g/cm$^3$ and a plateau rigidity modulus of less than 50,000 Pas. However, these compositions are foamed at the time of manufacture and stored in the desired containers. Drawbacks with this technology include the fact that during storage, and prior to use, the foam may lose its aeration so that it will not provide a thickening appearance.

Another type of foaming composition for application to keratinous fibers is taught in U.S. Pat. Nos. 7,837,984; 7,837,985; and 7,846,424. These compositions foam after extraction from the receptacle and upon application to the lashes. The advantage here is that the compositions will not lose aeration when stored. However the foaming is achieved with volatile blowing agents such as pentane, tetrafluoroethane, and the like. In many cases these types of solvents are not environmentally friendly. In addition, these types of compositions must be stored in separate chambers so that the reactants are separated, then combined immediately prior to use.

There is an ongoing need for a composition and method for application to keratinous fibers which provides the appearance of increased volume, where the increase in volume occurred immediately prior to use, where the composition containing all the ingredients could be maintained in a single receptacle, and where composition readily affixed to keratinous fibers in its increased volume state.

SUMMARY OF THE INVENTION

The present invention relates to a method of applying a cosmetic composition to hair, the method comprising a removing a cosmetic composition from a sealed container, the composition comprising: a post-foaming emulsion comprising a weak acid, a weak base, a fatty acid, and a volatile buffering agent; a film forming agent; and an aqueous carrier; applying said composition to one or more eyelashes; and during or after said application to said one or more eyelashes, said cosmetic composition forms a foam, said foam resulting from the release of a gas, said gas being a reaction product of said post-foaming emulsion, and said reaction commencing after the evaporation of said volatile buffering agent, upon exposure of said cosmetic composition to atmospheric conditions.

DETAILED DESCRIPTION

All percentages, ratios and proportions herein are by weight of the total cosmetic composition, unless otherwise specified. All temperatures are in degrees Celsius (° C.) unless otherwise specified.

As used herein, the term "comprising" means that other steps, ingredients, elements, etc. which do not affect the end result can be added. This term encompasses the terms "consisting of" and "consisting essentially of".

As used herein, the terms "foam" refers to a mass of small bubbles formed from the release of a gas. The foam described herein results from the reaction product the weak acid and weak base discussed hereinafter.

As used herein, the term "post-foaming emulsion" refers to a liquid composition that does not create a foam as it is dispensed from its container. Rather, the composition creates a foam after exposure to atmospheric pressure for at least 2 seconds. More specifically, the foam is a result of the reaction product of a weak acid and a weak base as described herein.

Post-Foaming Emulsion

The cosmetic composition herein comprises a post-foaming emulsion. The post-foaming emulsion is present in the composition at from about 1 to about 25 wt. % of the cosmetic composition. More preferably, the emulsion is present in the composition from about 3 to about 20 wt. %, and most preferably from about 5 to about 15 wt. % of the composition.

The post-foaming emulsion is formed by combining a buffering agent, which is preferably ammonium hydroxide, and a fatty acid to create an ammonium soap (ie. saponification), which effectively renders the fatty acid non-reactive in the presence of a weak base. The ammonium soap is then mixed with a weak base in a sealed container. The ammonium hydroxide is present in excess of the fatty acid component, such that the pH of the composition is maintained at a pH of at least about 7.5, preferably at least about 8.5, and most preferably at least about 9. The components are then emulsified under prop mixing, using, for example, a Caframo® BDC1850 mixer.

Suitable buffering agents include potassium hydroxide, sodium hydroxide, and ammonium hydroxide. Volatile buffering agents such as ammonium hydroxide are particularly preferred for the cosmetic compositions herein. The buffering agent is generally present in an amount of from about.

Suitable fatty acids include oleic acid, myristic acid, palmitic acid, and lauric acid. Stearic acid is also suitable, but may benefit from additional solvent to reduce the viscosity of stearic soap. In at least one embodiment, the fatty acid component is derived from beeswax fatty acids, which generally contains natural fatty acids of long chain alcohols. Such beeswax fatty acids are from white beeswax, available under the tradename White Beeswax Pastilles® SP 422P from The Sun Chemical Company, LTD.

The weak acid component is present in addition to the fatty acid component. And it distinctively is not a reactant during the saponification process. Suitable weak acids include citric acid, acetic acid, formic acid, lactic acid, oxalic acid, and mixtures thereof. The term "weak acid" as used herein, means an acid that dissociates incompletely in an aqueous solution.

The weak base component is present in addition to the buffering agent. And it distinctively is not a reactant during the saponification process. Preferably, the weak base is sodium bicarbonate. The term weak base, as used herein, means a base that does not ionize fully in an aqueous solution.

The post-foaming emulsion is stored in a hermetically sealed container. In use, the emulsion is dispensed from its container, and upon exposure to the atmosphere, the ammonium hydroxide evaporates. Upon evaporation, the pH drops, and the weak acid reacts with the sodium bicarbonate, liberating carbon dioxide gas (and water), creates a foam.

The components of the post-foaming composition may be present in any ratios or levels sufficient to enable foaming after exposure of the post-foaming emulsion to the atmosphere. Preferably, the weak acid, weak base, and buffering components are present at about a 1:1:5 ratio.

Other optional or additional ingredients discussed hereinafter are present in the composition only to the extent that they do not prevent, impede, or destabilize the formation of the reaction products of the post-foaming emulsion discussed herein.

Aqueous Carrier

The cosmetic compositions comprise an aqueous carrier. The level and species of the carrier are selected according to the compatibility with other components, and other desired characteristics of the product. Carriers useful in the present invention include water and water solutions of lows r alkyl alcohols. Lower alkyl alcohols useful herein are monohydric alcohols having 1 to 6 carbons, more preferably ethanol and isopropanol.

Preferably, the aqueous carrier is substantially, or entirely, water. Deionized water is preferably used. Water from natural sources containing mineral cations can also be used, depending on the desired characteristic of the product. Generally, the compositions comprise from about 20% to about 99%, preferably from about 40% to about 98%, and more preferably from about 60% to about 98% aqueous carrier.

Film Forming Agent

A film forming agent may be present in the cosmetic composition in an amount sufficient so that when the composition is applied to the hair of the scalp, eyebrows or eyelashes, and the cosmetic composition begins to foam, the film formed by the film forming agent will stabilize at least a portion of the foam (as will be elaborated on more fully below) thereby imparting a volumizing effect to the hair fibers upon which the composition is applied.

The film forming agent can be natural or synthetic. Film forming waxes are known in the art and can be employed alone or in combination with one or more natural or synthetic film forming agents. Synthetic film forming agents are particularly preferred. Conventional film forming agents, such as acrylates copolymers and/or methacrylates copolymers are suitable for the compositions herein. Suitable, non-limiting examples of film-forming agents include sodium acrylates copolymer, sodium acryloldimethyl taurate copolymer, ethyl methacrylate/N-butyl acrylate/2-methylhexyl acrylate copolymer, and butyl acrylate/hydroxyethyl methacrylate copolymer. Polymeric blends, such as Interpolymer's SYNTRAN® EX-100 and Kobo Product's DAI-TOSOL™ 5000 SJ are also useful as synthetic polymer film forming agents. Preferably, the film forming agent is employed in a concentration of from about 1 to about 50% by weight, more preferably about 5 to about 40% by weight, most preferably about 10 to about 30% by weight, and optimally about 15 to about 25% by weight, based on the total weight of the composition. As will be discussed below, the cosmetic composition may contain a pigment dispersion that includes one or more film forming agents, the amount of film forming agent contributed by the pigment dispersion is considered in the total amount of film forming agent in the cosmetic composition. For example, if the cosmetic composition contains 50 wt %, based on the total weight of the cosmetic composition, of a pigment dispersion that further contains 40 wt %, based on the total weight of the pigment dispersion, of a film forming agent, the cosmetic composition has 20 wt % film forming agent (due to the contribution of the pigment dispersion). Additional film forming agent may be added to a total of about 50 wt % based upon the total weight of the cosmetic composition.

Without being bound by theory, it is believed that during the post-foaming action, the film forming agent will set, thus, locking or sealing the foam lattice in place, either by forming a film, preferably a flexible film, over at least a portion of the surface of the foam or by increasing the rigidity of the foam lattice thereby stabilizing the foam. Preferably, a film will form over greater than about 50 percent of the surface of the foam, and more preferably over greater than about 75 percent of the surface of the foam. Alternatively, the film forming agent increases the rigidity of the foam lattice by greater than about 50%, and more preferably by greater than about 75%.

Since the compositions are preferably used as cosmetic compositions for application to the hair, eyebrow and eyelashes, it is preferred that the film forming agent is of the type and amount to allow the composition to be removed from the user with water, mild soap or a mild cosmetic cleanser.

Colorant

The cosmetic compositions may be transparent or colored. Preferably when it is to be applied to the eyelashes it is colored. The present invention incorporates colorants in amount sufficient to mask the color of the foam, which is usually white, so that when the compositions are applied to the hair, the colarant imparts a color other than white. The presence of the pigment in an amount sufficient to mask the color of the foam enhances the compositions' utility as cosmetic compositions, such as a mascara, a hair-volumizing dye or colorant or an eyebrow composition, among others. The cosmetic composition preferably includes about 0.5 to about 30% by weight, more preferably about 1 to 15% by weight, and most preferably about 2 to about 10% by weight, pigment based upon the total weight of the post foaming emulsion.

Preferably, the colorant is a pigment, and more preferably a pigment dispersion containing one or more film forming agents, which are preferably film forming polymers. The pigment dispersion is preferred because of the physical attributes associated with a finely dispersed, clump free, color solution providing added film forming capability. Dry pigments (Iron II, III oxide) may also be utilized and, when combined with the proper water-soluble polymeric film forming agents and properly dispersed, can accomplish the desired effect.

In one illustrative embodiment, the pigments are hydrophilic, which may include, but are not limited to pigments that are inherently hydrophilic (e.g., metal oxides) due to their polarity, or pigments (e.g., carbon black) that are surface-treated with a material so as to confer hydrophilicity. Pigment treatment materials that may confer hydrophilicity include silicone surfactants, such as oxyalkylenated silicones, PEG-dimethicones, dimethicone copolyol, alkyl-substituted dimethicone copolyols (e.g., cetyl or stearyl dimethicone copolyol); sulfopolyesters, such as those commercially available under the tradenames of Eastman AQ 14000 and Eastman AQ 55 from Eastman Chemical Company (Kingsport, Tenn.). The use of hydrophilic pigments may function to improve the re-wettability of the cosmetic compositions. For example, iron oxides surface-treated with PEG-9 dimethicone or decyl glucoside can be readily used in the present invention. Carbon black surface-treated with Eastman AQ 55 polymer can also be used for the practice.

The pigment is generally employed in an amount of from about 5 to about 50% by weight, based on the total weight of the composition. It should be appreciated that in lieu of the about 0.5 to about 15% by weight of pigment, the composition can contain from about 0.5 to about 90% by weight of a pigment dispersion comprised of polymeric film forming agents, pigment, emulsifier and other adjuvants.

Additional ingredients, such as vitamins, antioxidants, conditioning agents may also be incorporated into the present invention.

Structuring Agent

The cosmetic composition may include one or more structuring agents to increase the viscosity or thickness of the composition. If present, the structuring agents are preferably provided in a total amount ranging from about 0.1% to about 70%, and more preferably from about 0.5% to about 60%, by total weight of the composition. Examples of suitable structuring agents include, but are not limited to animal waxes, vegetable waxes, mineral waxes, various fractions of natural waxes, synthetic waxes, petroleum waxes, polyethylene waxes, polypropylene waxes, polyurethane waxes, hydrocarbon-based waxes such as Fischer-Tropsch waxes, silicone waxes, and mixtures thereof. Preferred other waxes in practice include beeswax, lanolin wax, shellac wax, carnauba wax, candelilla wax, bayberry wax, ozokerite, ceresin, paraffin, microcrystalline waxes, polyethylene waxes, C24-C45 methicones, and the like. Other types of structuring agents can also be used for increasing the viscosity or thickness of the cosmetic compositions, such as those having an HLB of from about 1 to about 8 and having a melting point of at least about 45° C.

Other suitable structuring agents may include saturated C14 to C30 fatty alcohols, saturated C16 to C30 fatty alcohols containing from about 1 to about 5 moles of ethylene oxide, saturated C16 to C30 diols, saturated C16 to C30 monoglycerol ethers, saturated C16 to C30 hydroxy fatty acids, C14 to C30 hydroxylated and nonhydroxylated saturated fatty acids, C14 to C30 saturated ethoxylated fatty acids, amines and alcohols containing from about 1 to about 5 moles of ethylene oxide diols, C14 to C30 saturated glyceryl mono esters with a monoglyceride content of at least 40%, C14 to C30 saturated polyglycerol esters having from about 1 to about 3 alkyl group and from about 2 to about 3 saturated glycerol units, C14 to C30 glyceryl mono ethers, C14 to C30 sorbitan mono/diesters, C14 to C30 saturated ethoxylated sorbitan mono/diesters with about 1 to about 5 moles of ethylene oxide, C14 to C30 saturated methyl glucoside esters, C14 to C30 saturated sucrose mono/diesters, C14 to C30 saturated ethoxylated methyl glucoside esters with about 1 to about 5 moles of ethylene oxide, C14 to C30 saturated polyglucosides having an average of between 1 to 2 glucose units and mixtures thereof, having a melting point of at least about 45° C. Preferred other structuring agents for practice are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred other structuring agents are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

Also useful as structuring agents, particularly in the aqueous phase of the compositions, are hydrophilic gelling agents such as the acrylic acid/ethyl acrylate copolymers and the carboxyvinyl polymers sold by the B.F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10-30 Alkyl Acrylate Crosspolymer). Combinations of the above polymers are also useful herein. Other gelling agents suitable for use herein include oleogels such as trihydroxystearin. Hydrophobically modified celluloses are also suitable for use as structuring agents. If present, the gelling agents are provided in a total amount ranging from about 0.05% to about 20%, and more preferably from about 0.5% to about 10%, by total weight of the composition.

Fibers

In some embodiments, the cosmetic composition may further include fibers for lash lengthening effects. The fibers useful in the present invention can be either natural fibers or synthetic fibers. Natural fibers include, but are not limited to: cotton fibers, silk fibers, wool fibers, and the like. Synthetic fibers include, but are not limited to: polyester fibers, rayon fibers, nylon fibers, and other polyamide fibers. If present, the fibers are preferably provided at an amount ranging from about 0.01% to about 10% by total weight of the composition.

Other Optional Ingredients

The cosmetic composition may also contain one or more hair care actives, such as hair straightening agents, hair curling agents, hair conditioning agents, hair growth agents, and the like. If present, such hair care actives may range from about 0.01% to about 50%, preferably from about 0.05% to about 35% by total weight of the composition.

The cosmetic composition may further include one or more humectants. If present, they may range from about 0.1 to 20% by weight of the total composition and include polyhydric alcohols including glycerol, C1-4 alkylene glycols such as butylene, propylene, ethylene glycol, glycerin, and the like, polyalkylene glycols, and alkylene polyols and mixtures thereof, hyaluronic acid, urea, sorbitol, sodium 2-pyrrolidone-5-carboxylate, soluble collagen, dibutylphthalate and gelatin.

A variety of water soluble preservatives can be added to the cosmetic compositions to provide a prolonged shelf life. Suitable preservatives include, but are not limited to: potassium sorbate, imidazolidinyl urea, p-hydroxy benzoate, esters of p-hydroxybenzoic acid, various parabens (as disclosed in the 12th Edition of CTFA's International Cosmetic Ingredient Dictionary and Handbook), ethylhexylglycerin, caprylyl glycol/phenoxyethanol/hexylene glycol, and the like. Other preservatives suitable for use in the cosmetic compositions are disclosed in the 12th Edition of CTFA's International Cosmetic Ingredient Dictionary and Handbook, the entire disclosure of which is herein incorporated by reference for all purposes. The cosmetic composition may optionally comprise a fragrance in an amount sufficient to make the composition more appealing to the consumer. Preferably, the fragrance is in the amount of from about 0.001% to about 10% by total weight of the composition.

Method of Cosmetically Treating Hair

The present invention provides a self-foaming composition, which when applied foams or swells to a specified volume. One application merely requires perhaps 2 to 6 brush strokes in order to achieve the desired volume. Most desirably, the composition is applied to the eyelashes and the composition contains a sufficient amount of a pigment to mask the natural color of the foam so that the resultant composition can be employed as a mascara which due to its volumizing effect imparts a thickened appearance to the eyelashes upon which the composition is applied.

Examples

| Ingredient | I | II | III |
|---|---|---|---|
| Deionized water | QS100 | QS100 | QS100 |
| Iron Oxide[1] | 6.00 | 2.00 | 3.50 |
| Hydroxyethylcellulose | 0.76 | 0.76 | 0.80 |
| PVP[2] | 2.00 | 2.00 | 1.50 |
| Talc | 0.01 | 0.01 | 0.02 |
| Ammonium Hydroxide | 3.25 | 4.25 | 3.50 |
| Aminomethyl Propanediol | 0.00 | 0.00 | 0.50 |
| Beeswax[3] | 2.30 | 2.30 | 2.50 |
| Stearic Acid | 3.80 | 3.80 | 3.00 |
| Glyceryl Stearate | 3.00 | 3.20 | 3.00 |
| Phenoxyethanol/caprylyl glycol/potassium sorbate/water/hexylene glycol (38:33:11:11:7) | 0.80 | 0.80 | 1.00 |
| Sodium Bicarbonate | 1.43 | 1.43 | 1.60 |
| Citric Acid | 3.57 | 3.57 | 3.48 |

[1]Black Iron Oxide C33-5198, available from Sun Chemical
[2]Polyvinylpyrrolidone solution (K-60, 45%), available from Sigma-Aldrich
[3]White Wax NF, Product Code SP-422, available from Strahl & Pitsch Inc.

A composition in accordance with the invention may be prepared as follows. All "parts" are based on percentage of total weight of the final composition.

1. Mix about 15 parts water and 6 parts iron oxide particles under a homogenizer (for example, from PRO Scientific) for 15-20 minutes in a main beaker ("vessel A").
2. Add 50 parts water to the vessel A.
3. Add hydroxyethylcellulose, slowly, to water under prop mixing. Mix for 15-20 minutes, then add to vessel A.
4. Add PVP and any aminomethyl propanediol to vessel A and stir for 5 min.
5. Add beeswax, stearic acid, glyceryl stearate, and Phenoxyethanol/caprylyl glycol/potassium sorbate/water/hexylene glycol into a support vessel ("vessel B") and heat/mix to 88° C.
6. Heat vessel A to 88° C. under prop mixing.
7. While vessel A and vessel B are heating, dilute 1.43 parts sodium bicarbonate in 4 parts water, in a support beaker ("vessel C").
8. While vessel A and vessel B are heating, prepare 3.57 parts citric acid, diluted in 5 parts water, in a support beaker ("vessel D").
9. When vessel A and vessel B are each at 88° C., mix the contents of vessel B into vessel A under a prop mixer until an emulsion is formed.
10. When emulsification is complete, mix under prop for an additional 15 minutes.
11. Remove vessel A from heat and air cool with prop mixing.
12. After vessel A reaches about 40° C., add the contents of vessel C to vessel A under a prop mixer.
13. Add the contents of of vessel D to vessel A under a prop mixer.
14. Finally, add any desired optional ingredients to vessel A (ie. fragrance, colorants/dyes, etc.).

We claim:

1. A method of applying a cosmetic composition to hair, the method comprising:
   a) removing a cosmetic composition from a sealed container, the composition comprising:
      i) a post-foaming emulsion comprising a weak acid, a weak base, a fatty acid, and a volatile buffering agent;
      ii) a film forming agent; and
      iii) an aqueous carrier;
   b) applying said composition to one or more eyelashes; and
   c) during or after said application to said one or more eyelashes, said cosmetic composition forms a foam, said foam resulting from the release of a gas, said gas being a reaction product of said post-foaming emulsion, and said reaction commencing after the evaporation of said volatile buffering agent, upon exposure of said cosmetic composition to atmospheric conditions.

2. A method according to claim 1, wherein said weak acid is selected from the group consisting of citric acid, acetic acid, formic acid, lactic acid, oxalic acid, and mixtures thereof.

3. A method according to claim 1, wherein said weak base is sodium bicarbonate.

4. A method according to claim 1, wherein said fatty acid is selected from the group consisting of oleic acid, myristic acid, palmitic acid, lauric acid, stearic acid, beeswax fatty acids, and mixtures thereof.

5. A method according to claim 1, wherein said volatile buffering agent is ammonium hydroxide.

6. A method according to claim 1, wherein said weak acid, weak base, and buffering agent are present at a ratio of about 1:1:5, respectively.

7. A method according to claim 6, wherein the pH of said composition is greater than about 7.5.

8. A method according to claim 1, wherein said post-foaming emulsion is present at from about 1 to about 25 wt. % of said composition.

9. A method according to claim 1, wherein said film forming agent is selected from the group consisting of sodium acrylates copolymer, sodium acryloldimethyl taurate copolymer, ethyl methacrylate/N-butyl acrylate/2-methylhexyl acrylate copolymer, butyl acrylate/hydroxyethyl methacrylate copolymer, and mixtures thereof.

10. A method according to claim 1, further comprising a colorant.

11. A method according to claim 10, wherein said colorant is selected from the group consisting of iron II oxide, iron III oxide, carbon black, and mixtures thereof.

12. A method according to claim 1, wherein said colorant is a pigment which is surface-treated with a material that confers hydrophilicity.

13. A method according to claim 1, further comprising one or more ingredients selected from the group consisting of vitamins, antioxidants, and conditioning agents.

14. A method according to claim 1, further comprising one or more additional ingredients selected from the group consisting of structuring agents and fibers.

15. A method according to claim 1, further comprising one or more hair care actives selected from the group consisting of hair straightening agents, hair curling agents, hair conditioning agents, hair growth agents, and mixtures thereof.

16. A method according to claim 1, wherein said cosmetic composition is provided as a mascara composition.

* * * * *